United States Patent
Brayton et al.

(10) Patent No.: US 6,193,743 B1
(45) Date of Patent: Feb. 27, 2001

(54) APPARATUS FOR MANUFACTURING AN ENDOCARDIAL DEFIBRILLATION LEAD WITH MULTI-LUMEN LEAD BODY AND METHOD

(75) Inventors: Dennis L. Brayton, Angleton; G. Shantanu Reddy, Houston; Alvin Coats, Angleton, all of TX (US)

(73) Assignee: Intermedics Inc., Angleton, TX (US)

( * ) Notice: Subject to any disclaimer, the term of this patent is extended or adjusted under 35 U.S.C. 154(b) by 0 days.

(21) Appl. No.: 09/252,403

(22) Filed: Feb. 18, 1999

(51) Int. Cl.[7] ........................................ A61N 1/00
(52) U.S. Cl. ................................................ 607/1
(58) Field of Search .................. 83/648; 269/8; 607/1, 122

(56) References Cited

U.S. PATENT DOCUMENTS

| | | | |
|---|---|---|---|
| 4,166,470 | 9/1979 | Neumann | 128/419 PG |
| 4,172,459 | 10/1979 | Hepp | 128/697 |
| 4,187,854 | 2/1980 | Hepp et al. | 128/419 PG |
| 4,815,469 | 3/1989 | Cohen et al. | 128/634 |
| 4,922,927 | 5/1990 | Fine et al. | 128/786 |
| 5,275,171 | 1/1994 | Barcel | 607/122 |
| 5,374,287 | 12/1994 | Rubin | 607/131 |
| 5,476,502 | 12/1995 | Rubin | 607/127 |
| 5,588,432 | 12/1996 | Crowley | 128/660.03 |
| 5,776,072 | 7/1998 | Hsu et al. | 600/518 |
| 5,840,031 | 11/1998 | Crowley | 600/440 |
| 5,871,508 | 2/1999 | Thompson et al. | 607/9 |
| 5,885,221 | 3/1999 | Hsu et al. | 600/515 |
| 6,004,269 | 12/1999 | Crowley et al. | 600/439 |
| 6,010,500 | 1/2000 | Sherman et al. | 606/41 |

*Primary Examiner*—William E. Kamm
(74) *Attorney, Agent, or Firm*—Schwegman, Lundberg, Woessner & Kluth, P.A.

(57) ABSTRACT

An implantable endocardial defibrillation lead having an elongated lead body with multiple lumens therein. Windows, cut through the lead body, provide access to selected ones of the lumens at selected locations along the lead body. In addition, a method and an apparatus for forming windows in a multilumen lead body are disclosed. A ferromagnetic stylet is inserted into a selected lumen. The lead body is oriented in a jig by application of an electromagnetic field. A grinder or punch cuts a window into the selected lumen.

8 Claims, 7 Drawing Sheets

APPARATUS FOR MANUFACTURING AN ENDOCARDIAL DEFIBRILLATION LEAD WITH MULTI-LUMEN LEAD BODY AND METHOD

BACKGROUND OF THE INVENTION

1. Field of the Invention

The present invention relates generally to implantable cardiac stimulation devices and systems for regulating the contraction of a heart. More particularity, the invention relates to a defibrillation lead, and more particularly to a defibrillation lead having multiple lumens therein and to a method of manufacturing for such leads.

2. Description of the Related Art

Implantable medical devices for treating irregular contractions of the heart with electrical stimuli are well known in the art. Some of the most common forms of such implantable devices are defibrillators and pacemakers.

Defibrillators are implantable medical devices used to treat fibrillation, a condition characterized by rapid, chaotic electrical and mechanical activity of the heart's excitable myocardial tissue that results in an instantaneous cessation of blood flow from the heart. Defibrillation is a technique employed to terminate fibrillation by applying one or more high energy electrical pulses to the heart in an effort to overwhelm the chaotic contractions of individual tissue sections and to restore the normal synchronized contraction of the total mass of tissue.

A pacemaker, or pacer, is an implantable medical device that delivers low energy electrical pulses to stimulate a patient's heart to beat at a desired rate in instances where the heart itself is incapable of proper self-regulation. This occurs when the heart's natural pacemaker, which causes the rhythmic electrical excitation of the heart and pumping of blood, malfunctions due to age or disease. Demand pacing is a process used to maintain normal beating of a heart having this condition.

Various types of leads for defibrillators and demand pacers have been suggested in the prior art. For example, large electrical patches sewn to the exterior surface of the heart have been used to deliver defibrillation pulses to the heart. Implantation of such patch electrodes requires opening of the patient's chest during thoracic surgery. For pacing, pulses may be applied to the heart with the use of a pacer lead having an exposed metal surface, or demand pacer electrode, extending through a vein and into the heart.

Those involved in the medical arts recognized that prior art defibrillators required a high threshold level of energy for effective defibrillation, which limited the useful life-span of the devices and, more significantly, posed a significant risk of causing electrolysis of the blood and myocardial damage. It was realized that the defibrillation electrode configuration played an important role in the amount of energy needed to achieve successful defibrillation. This led to the development of transvenous defibrillation leads having long coil-shaped defibrillation electrodes for implantation into the right ventricle of the heart through a vein. For example, U.S. Pat. No. 4,922,927, the entire disclosure of which is incorporated herein by reference, discloses a defibrillation electrode made up of a plurality of separate wires wound side-by-side to form a tight coil. The coil was disposed upon an insulated tubular member and had a length sufficient to extend throughout the entire length of the ventricular chamber to provide sufficient electrode surface area for defibrillation.

Transvenous cardiac stimulation leads, such as the device of U.S. Pat. No. 4,922,927, were configured to also carry a demand pacing electrode. Thus, a single device implantable in one surgical procedure could provide defibrillation and pacing pulses for heart patients suffering from both irregular heart beat and, at times, cardiac fibrillation. This eliminated the need for multiple and complex surgical procedures to attach the prior art electrodes required for both types of treatments.

Another defibrillation electrode configuration for use with dual purpose transvenous leads is disclosed in U.S. Pat. Nos. 5,476,502 and 5,374,287 to Rubin, which are also incorporated herein by reference in their entireties. The "Rubin" catheter included either a helical or lance shaped defibrillation electrode for delivering a defibrillation pulse directly to the interior of the septum of the patient's heart. The length of the helix-shaped electrode to be screwed into the septum from the right ventricle, about 0.5 cm to 1.0 cm, was substantially shorter than the conventional coiled transvenous defibrillation electrodes.

Despite these developments there continues to be a need for a lead capable of providing both high voltage defibrillation and effective demand pacing with a smaller lead diameter to minimize obstruction in the veins leading to the heart. One such lead has been developed by some of the inventors herein and others. A commonly-assigned patent application has been filed entitled Endocardial Defibrillation Lead with Looped Cable Conductors, attorney docket no. ITM-609 US, the disclosure of which is incorporated herein by reference. This lead has a looped cable conductor for conducting high voltage defibrillating shocks to the heart and a coil conductor for conducting low voltage pacing pulses. These two conductors are carried in separate lumens within a lead body. Additional lumens may be provided for additional conductors, if additional functions are desired. The conductors are connected to pacing or defibrillation electrodes or to sensors or other devices at selected locations along the length of the lead body. To connect the electrodes or other devices to a conductor, it is frequently necessary to cut a window through the lead body to gain access to a selected lumen. Because lead bodies are often made of silicon rubber and are very flexible, it is difficult to make these windows in a replicable fashion.

SUMMARY OF THE INVENTION

We have invented an implantable defibrillation lead with an elongated, flexible lead body having multiple lumens and windows at selected locations along the lead body, the windows providing access to selected lumens. We have also invented a method of manufacturing such leads and an apparatus for performing this method. According to our invention, a jig with an electromagnetic table supports a lead body. A ferromagnetic stylet, inserted in a selected lumen of the lead body orients the lead body in the jig when the lead body is placed within the magnetic field of the electromagnet. Mechanical grinding wheels then remove material at selected locations to form the windows. Alternatively, a punch could also form the windows.

In a preferred embodiment, there is provided an implantable endocardial defibrillation lead having a looped cable conductor for conducting at least high voltage defibrillation shocks. A coil electrode is connected to an elongated, flexible, electrically non-conductive lead body and is supplied with electrical power for delivering electrical shocks to the heart through a looped cable conductor that extends through the lead body and is associated with a power source.

Depending upon the desired application for the lead, the invention may also be used with a pacer and, thus, include any of a variety of pacer electrodes and sensors that are presently available or may become available. Such devices, if used, would be disposed upon the lead, insulated from the defibrillator electrode segments and electrically connected with a second electrical conductor that extends through the lead body and provides electrical power to the pacer electrode. The lead may also include a ground electrode disposed upon the lead a distance from the other electrodes to receive the pulses delivered to the heart tissue and transmit them back through a third electrical conductor extending through the lead. The coil electrode and looped cable conductor may also serve a dual function as a ground electrode and conductor.

The invention may also be adapted for fixation of the distal end of the lead to the heart to achieve selective positioning of the electrode or electrodes. A variety of currently available passive and active fixation mechanisms, or that may become available, may be used with the invention. In one embodiment of the invention, the lead includes tines. A small fixation screw for securing the distal end of the lead within the heart, wherein the fixation screw also functions as a pacer stimulating and sensing electrode, could be used.

The characteristics and advantages of the present invention described above, as well as additional features and benefits, will be readily apparent to those skilled in the art upon reading the following detailed description and referring to the accompanying drawings.

BRIEF DESCRIPTION OF THE DRAWINGS

For a detailed description of the preferred embodiments of the invention, reference will now be made to the accompanying drawings wherein.

DETAILED DESCRIPTION OF THE PREFERRED EMBODIMENT

The presently preferred embodiment of the invention are shown in the above-identified figures and described in detail below. In describing the preferred embodiments, like or identical reference numerals are used to identify common or similar elements. The figures are not necessarily to scale and certain features and certain views of the figures may be shown exaggerated in scale or in schematic form in the interest of clarity and conciseness.

Figure 1:
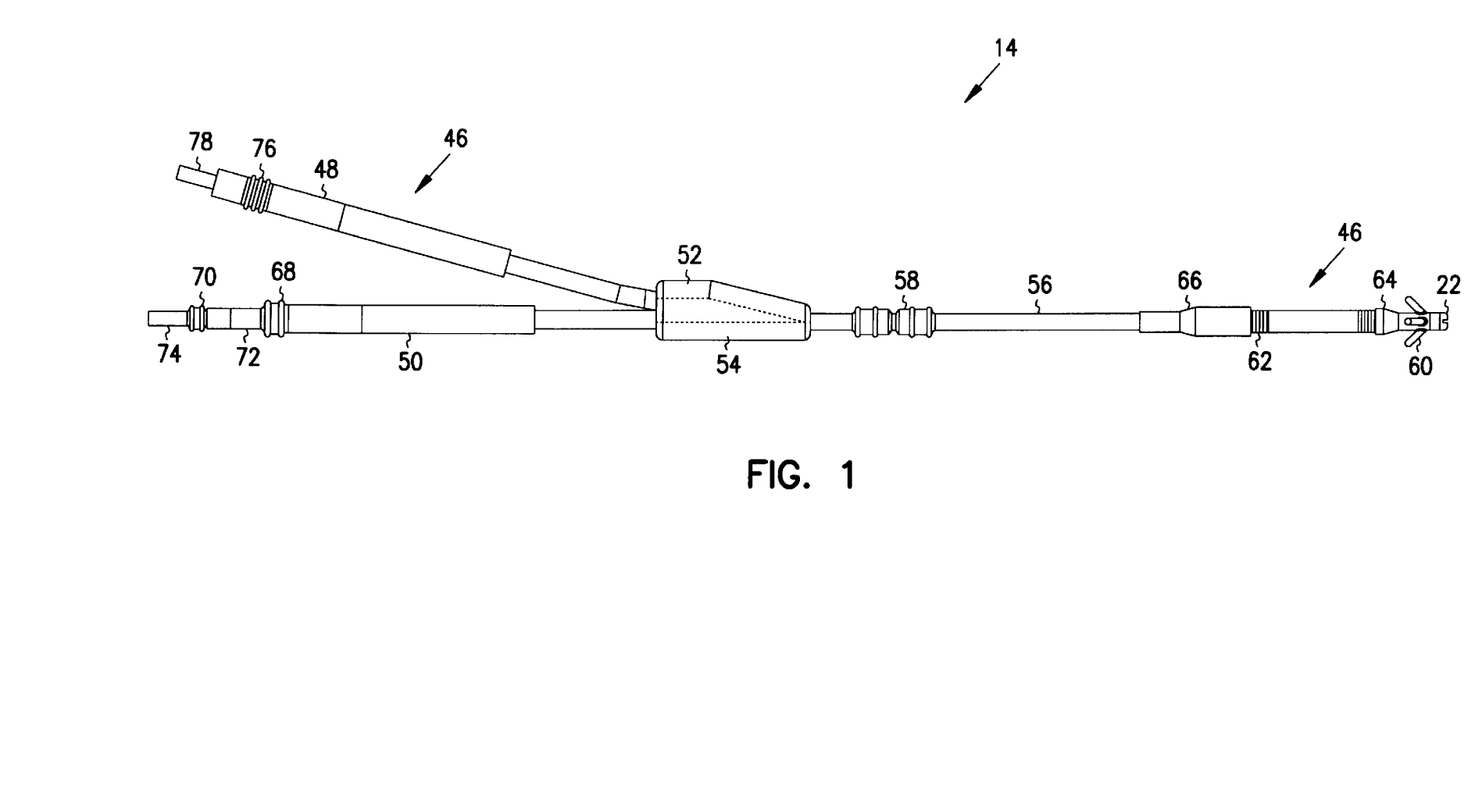
FIG. 1 is a plan view of an implantable defibrillation and pacing lead.

FIG. 1 illustrates a plan view of an endocardial high voltage cable lead 14. A ventricular tip cathode or electrode 22 and shock coil 24 are located at distal end 44 of the lead 14. At a proximal end 46 of the lead there is a high voltage connector 48 and a low voltage connector 50, preferably an IS-1 (international standard one) connector. The two connectors 48, 50 are joined at a junction 52 which is covered by an insulative boot 54. A lead body 56 extends between the distal end 44 and the proximal end 46. A suture sleeve 58 is slidingly received on the lead body 56 and conventionally provides additional support for the lead 14 where it is inserted in a blood vessel of a patient. At the tip cathode 22, tines 60 may be provided to help secure the lead 14 within the heart. Other well known active or passive fixation devices, such as helical screws, may be provided. Such features are well known in the art and need not be further described herein.

The shock coil 24 comprises a segment 62 of coiled wire, preferably multi-filar, more preferably tri-filar. A distal cap 64 secures one end of the segment 62, while a proximal sleeve 66 secures the other end. More detail concerning the shock coil 24 will be provided hereafter.

Regarding the proximal end 46 of the lead 14, the low voltage connector 50 is provided with annular sealing rings 68, 70 to prevent body fluids from injuring the connector, when the connector is inserted into the implantable device. Between the sealing rings 68, 70, a lead connector 72 may be provided. A pin connector 74 is located at the proximal end of the lead, thus providing two electrical contacts for the low voltage connector 50. Through these connectors 72, 74, the electrical condition of the heart may be sensed, particularly of the ventricle, if the distal end of the lead 14 is implanted therein. In addition, pacing pulses and other low voltage therapy may be provided through these connectors to the tip cathode 22. As will be more fully explained below, the shock coil 24 may be used as a low voltage anode or indifferent electrode if bipolar sensing or pacing is desired. Alternatively, a conventional low voltage ring electrode could be provided near the distal end of the lead.

The high voltage connector 48 also has annular sealing rings 76, but is usually provided only with a pin connector 78. The electrical path for high voltage shocks is usually between this pin connector 78 through an electrical conductor to the shock coil 24 and back through the heart to a can of the implantable medical device (not shown). However, an additional coiled electrode could be provided, forming a bipolar shock electrode. Where two coiled shock electrodes are used, they are frequently placed on the lead such that one would be in the ventricle and the other in the atrium or superior vena cava. Multi-filar coiled connectors have heretofore been used to conduct the electrical current for the shock to one or more shock coils.

Figure 2:
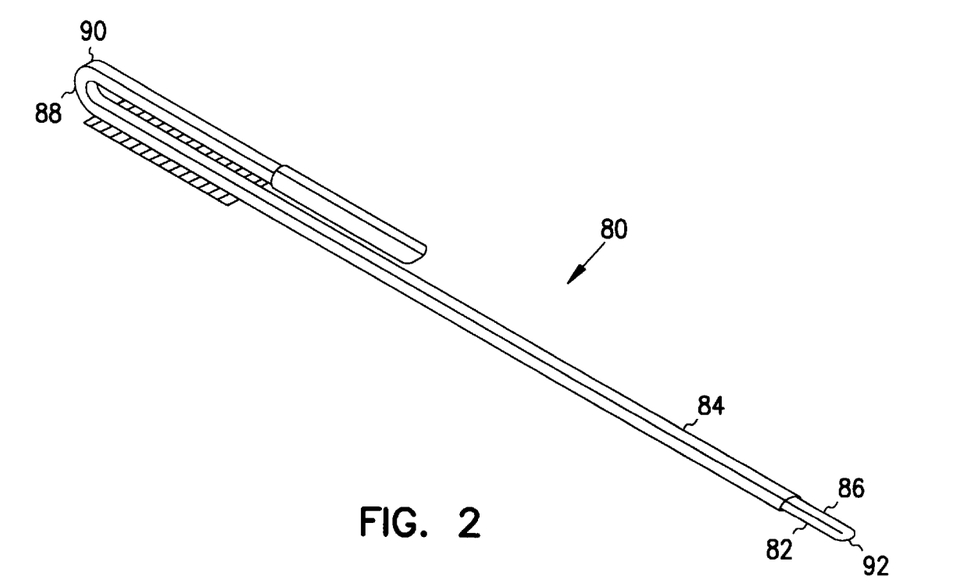
FIG. 2 is a perspective view of a cable conductor used in the lead.

In a preferred embodiment, a looped cable conductor is provided. The cable conductor 80 is illustrated in prospective view in FIG. 2. The cable conductor 80 comprises a conductive multi-strand wire 82. Preferably, most of the wire 82 has insulation 84. A middle section of the wire 86 is stripped of insulation, and then the cable conductor is folded back on itself, forming a loop or bend 92 at the middle section 86. Each end 88, 90, of the conductor is also stripped of insulation. As a consequence of the looped construction described, the conductor 80 forms a redundant system, as either side of the conductor is capable of carrying current to the shock coil 24.

Figure 3:
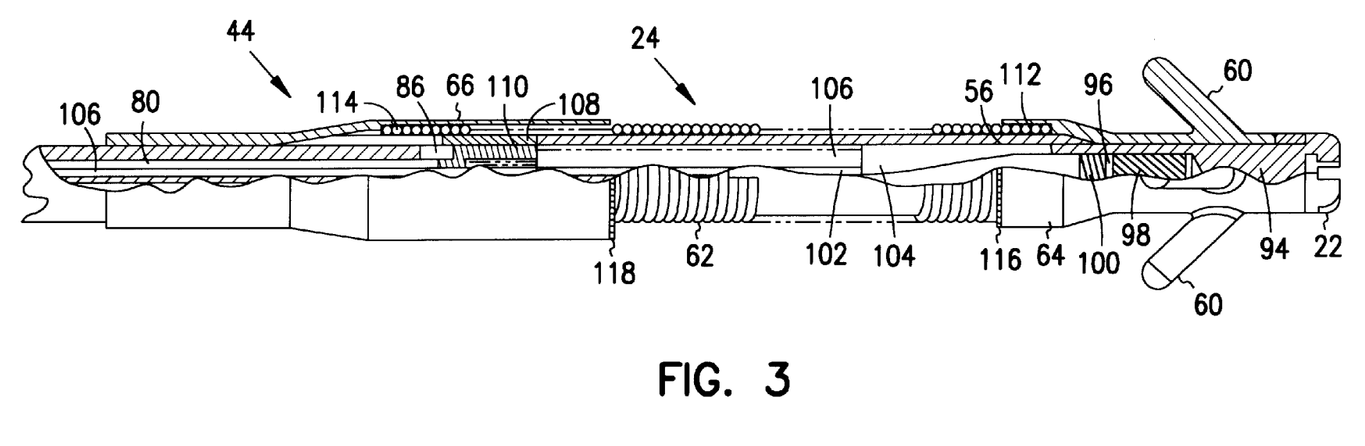
FIG. 3 is a partial section of a distal end of the lead of FIG. 1 with a window for allowing connection of a cable conductor to a defibrillation electrode.

We will describe the distal end 44 of the lead 14 in greater detail, in connection with FIG. 3. FIG. 3 is a partial through-section of the distal end 44. As can be seen in FIG. 3, the tip cathode 22 comprises a shank 94 which extends into the distal cap 64, and into the lead body 56. The tines 60 are formed on the distal cap 64. In addition, the distal cap 64 captures a distal end 112 of the coil segment 62. Within the shank 94, a stopped bore 96 receives a crimp plug 98 and a coil conductor 100. The coil conductor 100 is a conventional low voltage conductor which extends from the tip cathode 22 to the pin connector 74 and electrically couples the cathode 22 and the pin connector 74. The shank 94 is crimped over the crimp plug 98 to secure the conductor 100 between the crimp plug and the shank.

The coil conductor 100 passes through a first lumen 102 in the lead body 56. Preferably this lumen is non-coaxial, that is, it is offset from the axis of the lead body 56. However, to receive the shank 94 symmetrically with respect to the lead body, a stopped bore 104 is provided in the distal end of the lead body. This stopped bore is coaxial with the axis of the lead body itself. A second lumen 106 is provided to receive the looped cable conductor 80. Preferably, this lumen is also non-coaxial with respect to the lead body and may be smaller in diameter than the first lumen 102. Additional lumens may be provided where additional looped cables are connected to other electrodes, such as a second shock electrode.

A window 108 is cut through a portion of the lead body 56 to expose the second lumen 106. An apparatus and method for forming this window will be further discussed below. An arcuate crimp sleeve 110 fills this window 108 and captures the stripped middle section 86 of the cable conductor 80. A proximal end 114 of the coil segment 62 extends over the arcuate crimp sleeve 110 and is covered by the proximal sleeve 66. This proximal end 114 preferably extends for a plurality of loops proximal to the arcuate crimp sleeve; preferably two loops. In multi-filar coils, each filar should form the loops proximal to the arcuate crimp sleeve. This extension proximal to the crimp sleeve relieves mechanical stresses, and reduces the possibility of a mechanical failure adjacent the crimp sleeve. A circumferential bead of adhesive 116 seals the distal cap 64 to the coil segment 62 and underlying lead body 56. A similar adhesive bead 118 likewise seals the proximal sleeve 66 to the coil segment 62 and lead body 56.

Figure 4:
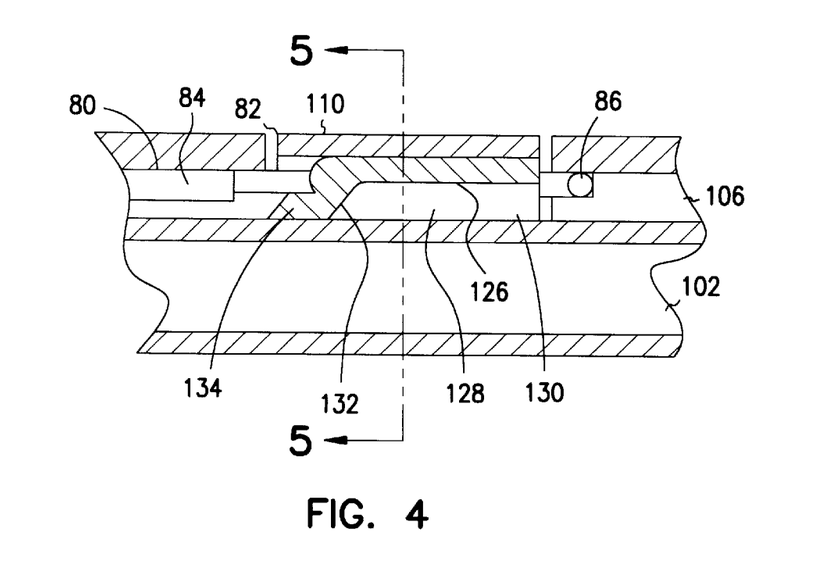
FIG. 4 is a plan view of the assembled inner sleeve and cable conductor at the window.
Figure 5:
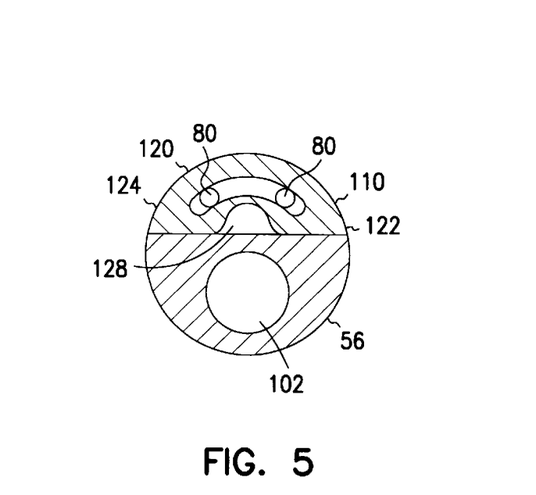
FIG. 5 is a through section of the window of FIG. 4, taken along line 5—5.

Further detail of the window and lumens can be seen in FIGS. 4 and 5. FIG. 4 is a top plan view of the window 108 with crimp sleeve 110, with the cable conductor 80 shown in phantom lines. FIG. 5 is a plan through section of the multilumen lead body.

Once the crimp sleeve 110 has been positioned in the lead body, the proximal sleeve 66 can be slid onto the lead body. The coiled segment 62 is then placed on the lead body with the proximal end extending past the crimp sleeve 110. The coil 62 is then laser welded to the crimp sleeve. The proximal sleeve 66 is brought up over the proximal end of the coil 62 and secured with adhesive, as described above.

Figure 6:
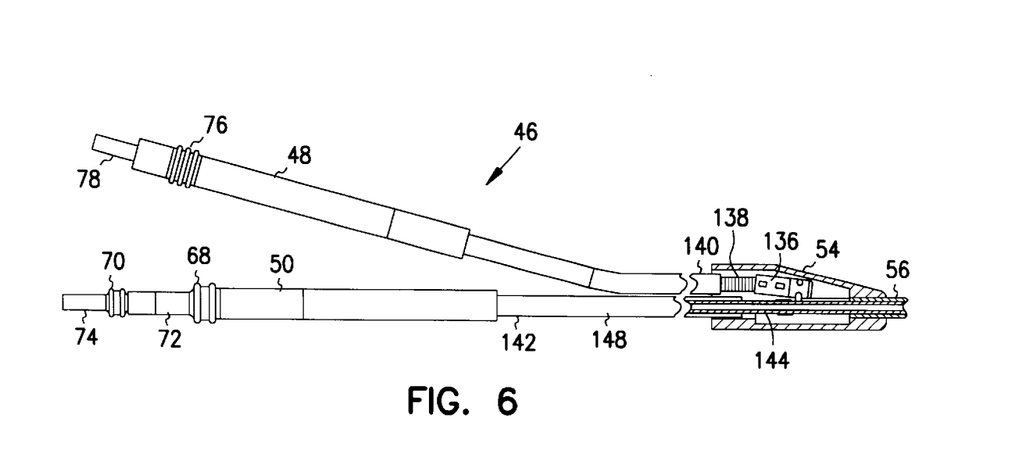
FIG. 6 is a partial through section of the proximal end of the lead.

The proximal end 46 of the lead is shown in FIG. 6, showing a partial through section of a plan view of the distal end 46 of the lead. The boot 54 encloses an assembly connecting the two connectors 48, 50. A crimp connector 136 is connected to a coiled conductor 138 which is electrically and mechanically connected to the pin connector 78 of the high voltage connector 48. The coil conductor 138 passes through an insulating sleeve 140. The low voltage connector 50 has a coaxial lead segment 142. The coil conductor 100, described above in connection with the distal end of the lead, passes co-axially down the lead segment 142, that is, the axis of the coil 100 and the axis of the lead segment 142 coincide. An inner tubing 144 surrounds the coil conductor 100. A return low voltage coil conductor 146 surrounds the inner tubing 144 and is connected proximally at one end to the ring connector 72 and at a distal end 150 to the crimp connector 136. An outer tubing 148 encases the return coil 146.

We will now describe an apparatus for preparing a window in the lead body 56. A cutting apparatus 150 is illustrated in perspective view in FIG. 7. A jig 152 is mounted on a base plate 153. The jig 152 has a sliding table 154 which holds a support beam 156 by means of end brackets 158,160. Machine screws 162 fasten the end brackets 158 to the table 154. Machine screws 164 connect the support beam 156 to the end brackets 158. A groove 166 runs longitudinally along the support beam 156 for receiving and supporting a lead body 56. Magnets 168 are mounted in the support beam 156 to attract a ferromagnetic stylet inserted in a lumen in the lead body. These magnets 168 are preferably fixed magnets but may also be electromagnets. Suitable fixed magnets are rare earth magnets available from Duracore. A back plate 170 mounted on the support beam 156 helps to prevent the lead from being displaced by the action of end cutter used to make a window in the lead body. In the illustrated embodiment, a slot 172 allows the cutter to pass through the back plate 170 during the cutting operation.

Figure 7:
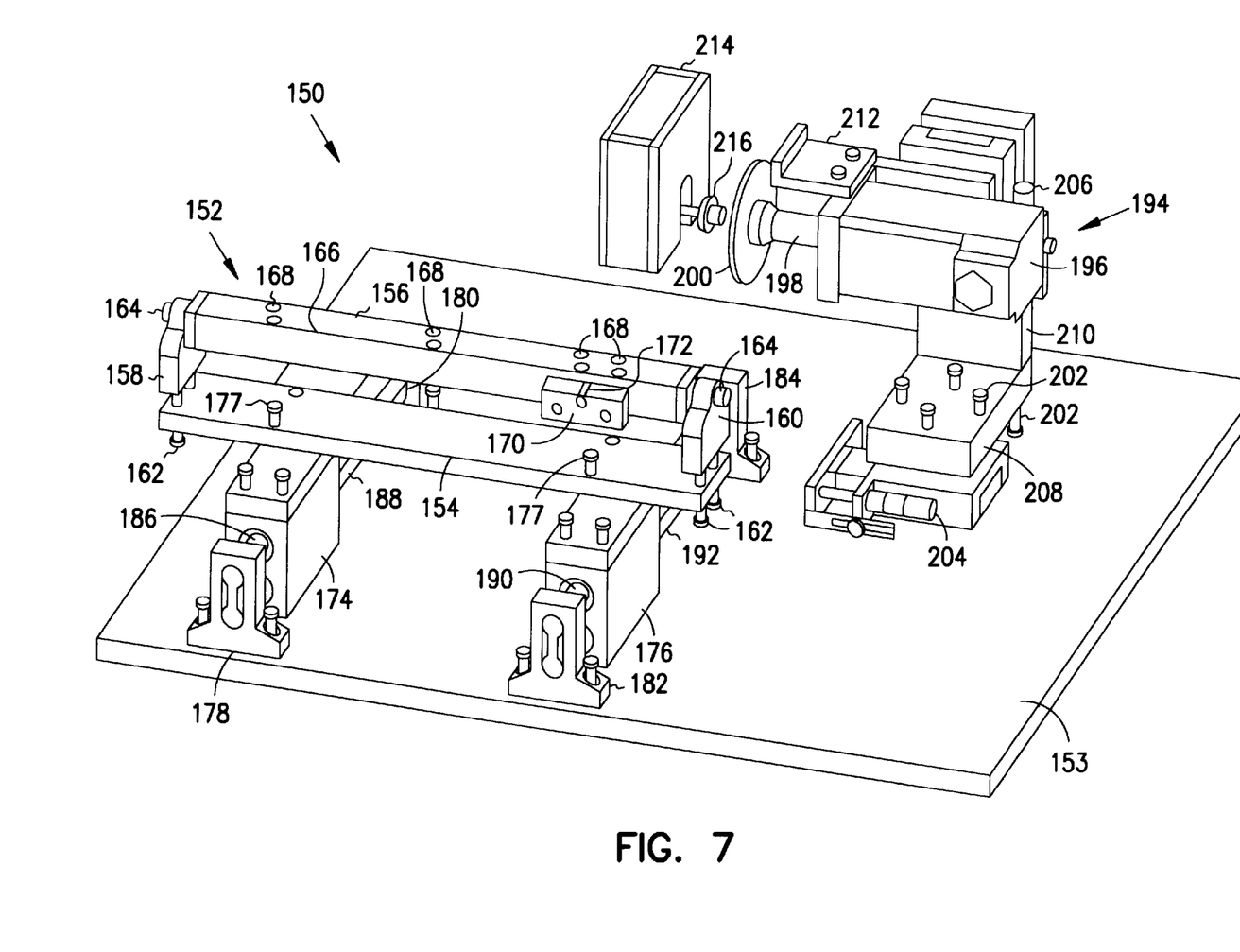
FIG. 7 is a perspective view of an apparatus for manufacturing windows in lead bodies according to the present invention.

Two ball bearing slides 174,176 support the table 154 which is fastened thereto by machine screws 177. The ball bearing slides 174, 176 are free to reciprocate smoothly between pillow blocks 178,180,182, 184 which support respective pairs of slide rods 186, 188 and 190,192. The ball bearing slides 174, 176 enable the jig 152 to be moved smoothly in a first linear direction which we will call the Z direction. This movement brings the lead body 56 into contact with a grinding wheel 200. The position of the grinding wheel 200 can be adjusted in two other mutually orthogonal directions which we will call X and Y directions, thus providing a complete range of adjustment for making the required window in the lead body 56. In our preferred embodiment, this cutter comprises a grinder 194. The grinder 194 comprises a grinder motor 196 which turns a shaft 198. The grinding wheel 200 is mounted on the end of this rotating shaft 198. The motor is supported by a motor mount 202 which has a horizontal micrometer 204 for adjusting the position of the grinding wheel 200 in the X or horizontal direction. A vertical micrometer 206 is also provided for adjusting the position of the grinding wheel 200 in a vertical or Y direction. A base 208 is fastened to the horizontal micrometer 204 and supports an upright mounting plate 210. In its turn, the upright mounting plate 210 supports the vertical micrometer 206 which is attached to the motor 196. As a safety feature, a shield 214 is mounted to a shield bracket 212 which shield bracket is also connected to the motor 196. A live center 216 rides against the end of the shaft 198 to reduce vibration.

In operation, a lead body is placed in the groove 166. The position of the grinding wheel 200 is carefully adjusted using the horizontal and vertical micrometers 204, 206. With the grinding wheel spinning 200, the table supporting the support beam 156 slides horizontally in the Z direction, thus causing the lead body 56 to pass under the grinding wheel 200 and cutting the desired window in the lead body. The lead body is properly oriented by the action of the magnets 168 on the ferromagnetic stylet in the lead body 56.

Figure 8:
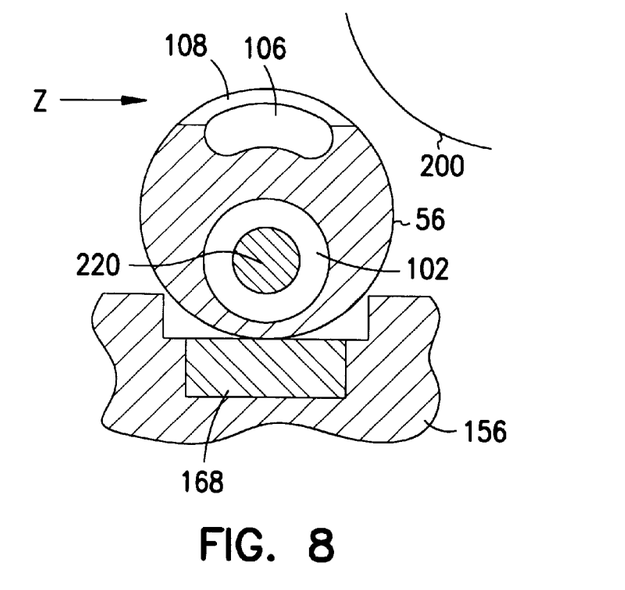
FIG. 8 is a cross sectional view of a multilumen lead and ferromagnetic stylet according to our invention.

This can be seen more clearly in FIG. 8 which shows a lead body 56 in cross section mounted on the support beam 156. The ferromagnetic stylet 220 is in the first lumen 102. The second lumen 106 is oriented properly by action of the magnet 168 on the ferromagnetic stylet 220. Sliding the table 154 in the Z direction shown brings the lead body 56 into contact with the grinding wheel 200, cutting the window 108.

Figure 9:
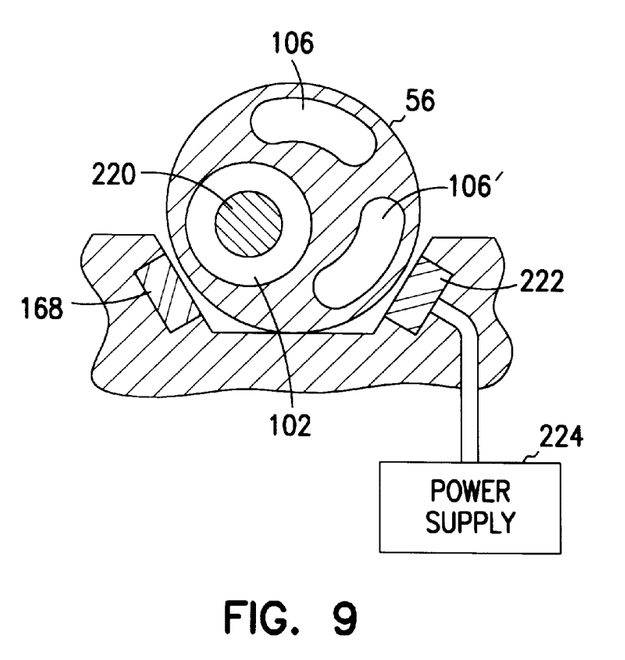
FIG. 9 is a cross sectional view as in FIG. 8, showing two magnets.

An alternative configuration is illustrated in cross section in FIG. 9. In FIG. 9 the lead body 56 is shown oriented toward the magnet 168 by magnetic action on the ferromagnetic stylet 122 such that the second lumen 106 may be cut by the cutter. A second magnet 222 is also provided. This magnet 222 is preferably an electromagnet connected to a power supply 224. Of course, electromagnets could be used for both first and second magnets. When the electromagnet 222 is activated, the ferromagnetic stylet 220 responds to both magnetic fields and readjusts the position of the lead body 56 such that a third lumen 107 can be cut. Of course, if an electromagnet is also used for the first magnet 168, that magnet may be turned off when the second magnet 222 is turned on.

Figure 10:
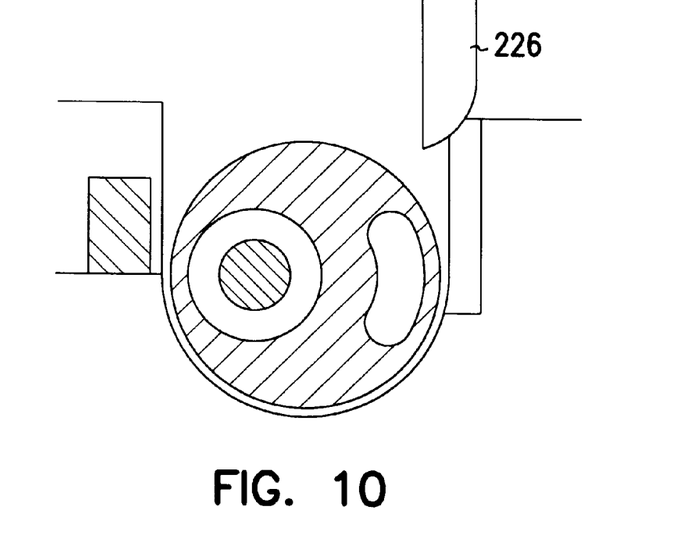
FIG. 10 is a cross sectional view as in FIG. 8, showing a punch.
Figure 11:
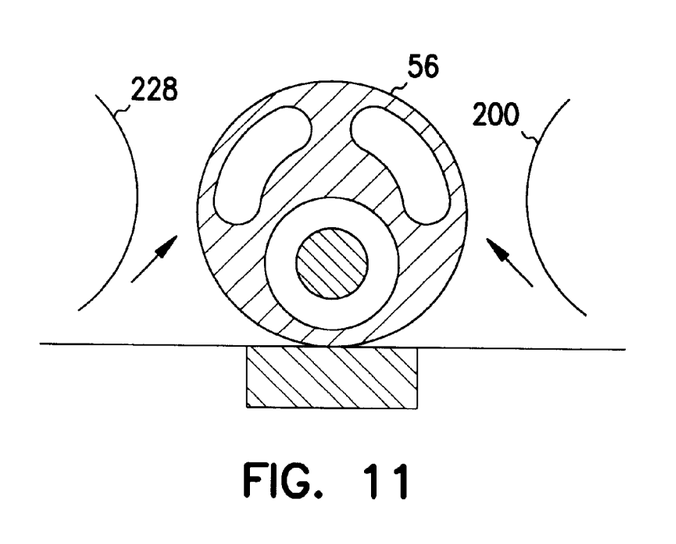
FIG. 11 is a cross sectional view as in FIG. 8, showing two cutters.

It will be recognized that other types of cutters may be used in place of a grinder wheel 200. For example, a punch 226 or knife edge could be utilized as illustrated in FIG. 10. In addition, multiple cutters could be utilized as illustrated in FIG. 11. The cutters may be made movable rather than the table 154, allowing windows to be cut in different lumens without reorienting the lead body 56. Alternatively, it may be desired to cut more than one window into the same lumen. Multiple parallel cutters would allow such an operation to be done in a single step.

Those skilled in the art will recognize from the foregoing description that the multilumen lead with windows of our invention can be used in cardiac leads in other configurations without departing from the teachings of our invention. For example, more then one looped cable conductor could be provided for bipolar defibrillation shocks. Low voltage connections could be provided to some, all or none of such looped cable conductors.

While preferred embodiments of the present invention have been shown and described, modifications thereof can be made by one skilled in the art without departing from the spirit or teachings of this invention. The embodiments described herein are exemplary only and are not limiting. Many variations and modifications of this system and apparatus are possible and are within the scope of the invention. Accordingly, the scope of protection is not limited to the embodiments described herein, but is only limited by the claims which follow, the scope of which shall include all equivalents of the subject matter of the claims.

What is claimed is:

1. An apparatus for cutting windows into at least one lumen of a lead body having multiple lumens therein, the apparatus comprising a jig for supporting an elongated, flexible lead body;

a magnetic field generator mounted at a selected orientation with respect to said jig, where the magnetic field generator is adapted to attract a stylet in one of the multiple lumens of the lead body; and a cutter mounted at a selected orientation with respect to said jig for cutting said window.

2. The apparatus according to claim 1 wherein said cutter comprises a grinder.

3. The apparatus according to claim 1 wherein said cutter comprises a punch.

4. The apparatus according to claim 1 wherein said magnetic field generator comprises an electromagnet.

5. The apparatus according to claim 1 further comprising a second magnetic field generator.

6. The apparatus according to claim 1 further comprising a second cutter mounted at a second selected orientation with respect to said jig for cutting a second window in said lead body.

7. The apparatus of claim 1, where the cutter includes a micrometer to adjust the selected orientation of the cutter with respect to the jig.

8. The apparatus of claim 1, including the stylet, where the stylet is sized to fit in at least one of the lumens of the lead body.

* * * * *